US008680081B2

(12) United States Patent
 Van Patten

(10) Patent No.: US 8,680,081 B2
(45) Date of Patent: Mar. 25, 2014

(54) PROPHYLACTIC TREATMENT OF MIGRAINE

(76) Inventor: Peter Van Patten, Aurora, MN (US)

( * ) Notice: Subject to any disclaimer, the term of this patent is extended or adjusted under 35 U.S.C. 154(b) by 1208 days.

(21) Appl. No.: 10/363,079

(22) PCT Filed: Aug. 27, 2001

(86) PCT No.: PCT/US01/26797
 § 371 (c)(1),
 (2), (4) Date: Feb. 27, 2003

(87) PCT Pub. No.: WO02/17896
 PCT Pub. Date: Mar. 7, 2002

(65) Prior Publication Data
 US 2003/0212050 A1     Nov. 13, 2003

Related U.S. Application Data

(60) Provisional application No. 60/228,851, filed on Aug. 29, 2000.

(51) Int. Cl.
 *A61K 31/60*  (2006.01)
 *A61K 31/415*  (2006.01)
(52) U.S. Cl.
 USPC ........................................... 514/165; 514/405
(58) Field of Classification Search
 USPC ........................................ 514/165, 406, 405
 See application file for complete search history.

(56) References Cited

U.S. PATENT DOCUMENTS

| | | | |
|---|---|---|---|
| 5,344,991 A | 9/1994 | Reitz et al. | 568/34 |
| 5,380,738 A | 1/1995 | Norman et al. | 514/374 |
| 5,434,178 A | 7/1995 | Talley et al. | 514/406 |
| 5,466,823 A | 11/1995 | Talley et al. | 548/377 |
| 5,474,995 A | 12/1995 | Ducharme et al. | 514/241 |
| 5,510,368 A | 4/1996 | Lau et al. | 514/419 |
| 5,585,504 A | 12/1996 | Desmond et al. | 549/323 |
| 5,604,260 A | 2/1997 | Guay et al. | 514/605 |
| 5,633,272 A | 5/1997 | Talley et al. | 514/378 |
| 5,872,145 A | 2/1999 | Plachetka | 514/415 |
| 6,060,499 A | 5/2000 | Plachetka | 514/415 |
| 6,063,811 A | 5/2000 | Hancock et al. | 514/473 |
| 6,136,804 A | 10/2000 | Nichtberger | |
| 6,136,839 A | 10/2000 | Isakson et al. | 514/406 |
| 6,217,877 B1 | 4/2001 | Weidner | 424/195.1 |
| 6,245,802 B1 * | 6/2001 | Iyengar et al. | 514/438 |
| 6,511,968 B1 | 1/2003 | Nichtberger | |

FOREIGN PATENT DOCUMENTS

| | | |
|---|---|---|
| EP | 1 064 948 | 1/2001 |
| EP | 1 064 966 | 1/2001 |
| WO | WO 98/17292 | 4/1998 |
| WO | WO 98/20870 | 5/1998 |
| WO | WO99/18960 * | 4/1999 |
| WO | WO 99/21585 | 5/1999 |
| WO | WO 00/25779 | 5/2000 |
| WO | WO 00/29022 | 5/2000 |
| WO | WO 00/48583 | 8/2000 |

OTHER PUBLICATIONS

Buring et al., JAMA, 1990;264(13):1711-1713.*
Grazzi et al., The Italian Journal of Neurological Sciences, 1995;16:577-586.*
Simon et al., Arthritis & Rheumatism, 1998;41(9):1591-1602.*
Von Seggern et al., "Rofecoxib in the Prevention of Perimenstrual Migraine: An Open-Label Pilot Trial", Headache, Feb. 2004, pp. 160-165.
Thorogood, "Risk of Stroke in Users of Oral Contraceptives", *JAMA Websites*, vol. 281, No. 14, Apr. 14, 1999, pp. 1255 (3 pages).
Lipton, et al., "Is Migraine a Progressive Brain Disease?", *JAMA Websites*, vol. 291, No. 4, Jan. 28, 2004, pp. 493 (3 pages).
Kruit et al., Table 1, Table 2, Table 3, Table 4, *JAMA Websites*, vol. 291, No. 4, Jan. 28, 2004, pp. 427 (4 pages).
Kruit et al., "Migraine as a Risk Factor for Subclinical Brain Lesions", *JAMA Websites*, vol. 291, No. 4, Jan. 28, 2004, pp. 427 (12 pages).
Buring, et al., "Low-dose aspirin for migraine prophylaxis", Abstract from *JAMA Websites*, vol. 264, No. 13, Oct. 3, 1990, p. 1711 (2 pages).
"Some migraines linked to brain disease", by Reuters, New York Times Jan. 28, 2004 : A20 (col. 5).
Deseo, Jennifer, "*Arthritis Drug May Help Migraine Sufferers*", New York, Jul. 2004 (Reuters Health)—http://www.euromeds.co.uk/information-on-vloxx.htm#pr6 (2 pages).
Davis, Jeanie Lerche, "*Arthritis Drug May Help Migraines*", WebMD Medical News Archive, Jun. 29, 2001, http://my.webmd.com/content/article/33/1728 (2 pages).
"*VIOXX® Relieved Acute Migraine Pain in a New Investigational Study of Patients with Migraine Headaches of Moderate to Severe Intensity*" Honolulu, Apr. 3, 2003, Newsroom Research & Development News, http://www.merck.com/newsroom/press_releases/research_and_development_news.html (3 pages).
John L Wallace and Mark J.S. Miller. "Nitric Oxide in Mucosal Defense: A Little Goes a Long Way", Gastroenterology, vol. 119, No. 2, Aug. 2000, pp. 512-520.
John L. Wallace, Louis J. Ignarro and Stefano Fiorucci, "Potential Cardioprotective Actions of No-Releasing Aspirin", Nature Reviews, vol. 1, May 2002. pp. 375-382.

(Continued)

*Primary Examiner* — San-Ming Hui
(74) *Attorney, Agent, or Firm* — Kagan Binder, PLLC

(57) ABSTRACT

The present invention provides methods and compositions for the prophylactic or targeted prophylactic treatment of migraine. In one embodiment a patient is regularly given a therapeutically effective amount of a combination of a cyclooxygenase-2 inhibitor and acetylsalicylic acid or active derivative, for prophylactic treatment of migraine. In another embodiment, a patient, at a time prior to a determined time window, is administered a therapeutically effective amount of a cyclooxygenase-2 inhibitor, either alone or in combination with acetylsalicylic acid or active derivative, to prevent or reduce migraine symptoms during the time window. Representative compositions include a cyclooxygenase-2 inhibitor and acetylsalicylic acid or salicylate salt.

31 Claims, No Drawings

(56) References Cited

OTHER PUBLICATIONS

Fiorucci et al., "NCX-4016 (NO-Aspirin) Inhibits Lipopolysaccharide-Induced Tissue Factor Expression In Vivo, Role of Nitric Oxide", Circulation, vol. 106. Dec. 10, 2002. pp. 3120-3125.
Fiorucci et al., "Gastrointestinal Safety of NO-Aspirin (NCX-4018) in Healthy Human Volunteers: A Proof of Concept Endoscopic Study", Gastroenterology, vol. 124. No. 3, Mar. 2003, pp. 600-607.
Fiorucci et al., "Gastrointestinal Safety of Nitric Oxide-Derived Aspirin Is Related to Inhibition of ICE-like Cystelne Proteases in Rats". Gastroenterology, vol. 116, No. 5, May 1999, pp. 1089-1106.
Wallace et al., "Anti-Thrombotic Effects of a Nitric Oxide-Releasing, Gastric-Sparing Aspirin Derivative", Journal of Clinical Investigation, vol. 96, 1995, pp. 2711-2718.
Virginia Byers Kraus, "Cyclooxygenase-2 Inhibitors and nonsteroidal anti-inflammatory drugs in the management of arthritis", Foot Ankle Clin N Am, vol. 8, 2003, pp. 187-200.
P.S. Gardiner and J.F. Gilmer, "The medicinal Chemistry Implications of the Anticancer Effects of Aspirin and Other NSAIDs", Mini Reviews in Medicinal Chemistry, vol. 3, No. 5, 2003, pp. 461-470.
David A. Peura, "Mandate to modify a medicinal mantra: Maybe not yet?", Gastroenterology, vol. 124, No. 3, Mar. 2003, 2 pages.
Raul Altman, "Acute coronary disease Athero-Inflammation: Therapeutic approach", Thrombosis Journal, vol. 1, No. 2, Jun. 20, 2003, pp. 1-6.
Fiorucci et al., "Interaction of a selective cyclooxygenase-2 inhibitor with aspirin and NO-releasing aspirin in the human gastric mucosa". PNAS, vol. 100. No. 19, Sep. 16, 2003, pp. 10937-10941.
NiCox Press Release, "Clinical results show NicOx's NCS-4016 maintains excellent gastric safety in co-administration with celecoxib", May 21, 2003 Sophia Antipolls, France (2 pages).
NiCox Press Release, "Merck & Co., Inc. and NicOx form research collaboration on Nitric Oxide-donating drugs", Aug. 19, 2003, Sophia Antlpolls, France (1 page).
Fiorucci et al., "Interatction of a selective cyclooxygenase-2 inhibitor with aspirin and NO-releasing aspirin in the human gstsic mucosa", Abstract from Proc Nail Mad Sci USA, Sep. 5, 2003.
Von Seggern et al., "An open-label trial of rofecoxib in the preventive treatment of peri-menstrual migraine" Headache—the Journal of Head and Face Pain, vol. 40, No. 5, May 2000, p. 436.
Merck Research Laboratories, "VIOXX Gastrointestinal Outcomes Research Study (VIGOR)", Feb. 8, 2001, pp. S1-S5 (synopsis), 64-71 and 100-104.
Pharmacia Pfizer, "Celebrex celecoxib capsules", Aug. 2002, 12 pages.
Merck & Co., Inc., "VIOXX rofecoxib tablets and oral suspension", Apr. 2002, 16 pages.
Pharmacia Pfizer, "Bextra valdecoxib tablets", Oct. 2002, 14 pages.

FDA Advisory Committee Briefing Document, NDA 21-042, s0007, VIOXX Gastrointestinal Safety, Feb. 8, 2001, 27 pages.
James E. Dalen, "Selective COX-2 Inhibitors, NSAIDs, Aspirin, and Myocardial Infarction", Arch Intern Med, vol. 162, May 27, 2002, pp. 1091-1092.
Raul Altman et al., "Efficacy Assessment of Meloxicam, a Preferential Cyclooxygenase-2 Inhibitor, in Acute Coronary Syndromes Without ST-Segment Elevation", Circulation, 106 (2): 191.
Raul Altman et al., "Role of Anti-Inflammatory Drugs in the Treatment of Acute Coronary Syndromes, From Athero-Inflammation to Athero-Thrombosis", Revista Espanola de Cardiologia, Editorials, vol. 56, Issue 1, Jan. 2003.
Clotam® Rapid, downloaded from http://emc.medicines.org.uk/medicine/449/spc/clotam+rapid/, 6 pages.
Eastham, R.D., "The low dose aspirin controversy solved at last?", British Medical Journal, vol. 291, Sep. 14, 1985, pp. 738-739.
EC-NAPROSYN®, 2010 Physician's Desk Reference, pp. 2850-2855.
Greer, IA, "The low dose aspirin controversy solved at last?", British Medical Journal, vol. 291, Nov. 2, 1985, 2 pages.
Henriksson, Peter et al., "Aspirin all round?", British Medical Journal, vol. 296, Apr. 2, 1988, 1 page.
Ketoprofen, Micromedex Drugdex® Evaluations, downloaded from http://www.westlaw.com, 223 pages.
Pederson, Anders K. et al., "Dose-Related Kinetics of Aspirin, Presystemic Acetylation of Platelet Cyclooxygenase", The New England Journal of Medicine, vol. 311, No. 19, Nov. 8, 1984, pp. 1206-1211.
Rimon, Gilad et al., "Coxibs interfere with the action of aspirin by binding tightly to one monomer of cyclooxygenase-1", Proceedings of the National Academy of Sciences of the United States of America, Jan. 5, 2010, vol. 107, No. 1, ISBN/ISSN:0027-8424-1, 6 pages.
"Diagnosis and Treatment of Primary Headache Disorders and Their Complications", *Wolff's Headache and Other Head Pain*. Ed. Stephen D. Silberstein, MD, FACP, Richard B. Lipton, MD and David W. Dodick, MD, FRCP(C), FACP. New York: Oxford university Press, 2008, 8$^{th}$ Edition, 205, 258.
Wolff's Headache and Other Head Pain, 7$^{th}$ Ed., Edited by Stephen D. Silberstein et al., 2001, p. 156.
Anthony, Michael et al., "Indomethacin in Migraine", The Medical Journal of Australia, vol. 1—55$^{th}$ Year, No. 2, Jan. 13, 1968, pp. 56-57.
Bensenor et al., "Low-Dose Aspirin for Migraine Prophylaxis in Women." *Cephalalgia. An International Journal of Headache.* Apr. 2001; 21(3): 175-183.
Hosman-Benjaminise, S.L. and Bolhuis, P.A. "Migraine and Platelet Aggregation in Patients Treated with Low Dose Acetylsalicylic Acid" *Headache* (1986); 26: 282-284.

* cited by examiner

PROPHYLACTIC TREATMENT OF MIGRAINE

REFERENCE TO RELATED APPLICATION

This application claims priority to PCt Application No. PCT/US 01/26797, filed Aug. 27, 2001 and entitled "Method of Treating Migraines and Pharmaceutical Compositions," the entire disclosure of which is hereby incorporated by reference; and which claimed the benefit of U.S. Provisional Application 60/228,851, filed Aug. 29, 2000, the entire disclosure of which is hereby incorporated by reference.

TECHNICAL FIELD

The present invention relates to prophylactic or targeted prophylactic treatment of a migraine condition, and compositions for prophylactic treatment of a migraine condition.

Migraine is among the most common of medical problems. Some people have migraine attacks often, while for others the migraine attacks occur infrequently. Migraine is a chronic and recurrent condition which often, but not always, involves a headache as part of a neurological symptom complex. These chronic recurrent symptoms often include phonophobia, photophobia, nausea and/or vomiting, disorientation, difficulty concentrating, and the urge to sleep. Some patients will experience other symptoms before, after, or during the development of a full-fledged migraine. These symptoms of migraine can also be difficult and distressing for the patient and may occur with or without headache. The symptoms are usually worsened by movement or exertion, and they are, in most moderate or severe attacks, quite distressing and oftentimes disabling for affected individuals. The features of a headache associated with a migraine attack are not distinctive, but the headache may involve throbbing, and it can be unilateral, bilateral, or diffuse. The other listed migraine attack and subsequently listed migraine aura symptoms may occur without headache, and the latter are particularly common in individuals over 50 years of age.

Some estimate that 20 million or more Americans have migraine. Migraine usually begins between the ages of 10 and 40, but it can begin at any age between infancy and the seventh decade. Most studies show a female preponderance of 60-70%. Migraine often remits or changes character during the sixth decade of life. Greater than one-half of afflicted individuals have a positive family history of migraine. The mechanism for migraine has not been well defined, although a number of theories have been advanced. Migraine may result from the response of a patient to the interaction of a number of factors including inherited susceptibility. Predisposing factors may include increasing or remitting stress (or emotional upset), hormonal factors including estrogen, certain medications, glare, skipped meals, and numerous dietary factors, including consumption of aged cheeses, aspartame, citrus, and alcoholic beverages (such as, for example, red wine).

There is no reliable, economically practical laboratory test available to aid the clinician in the diagnosis of migraine. However, there are some characteristic features of a migraine attack which are often helpful. Several hours or days before the migraine attack begins (a period called the "prodrome"), symptoms of a change in mood, irritability, fatigue, yawning, or a change in appetite occur in 40 to 60% of migraine patients. About 20% of migraine patients have dysphasia or lose vision in a specific area (called a "scotoma") or see jagged, shimmering, or flashing lights. This period is called the "aura," and it usually appears gradually over 5 to 20 minutes, with a 20 to 40 minute expansion, spread, or build-up in the case of a visual aura. Less commonly, images are distorted; for instance, objects appear smaller or larger than they are. Some patients experience tingling sensations or, rarely, weakness in an arm or leg. Usually these symptoms disappear shortly before a migraine-related headache begins, but sometimes they merge with it. The pain of a headache associated with a migraine attack may be felt on either side of the head or over the entire head. Occasionally, the hands and feet may become cold and turn blue. In most of those who have a prodrome, the pattern and headache location remain essentially the same with each migraine attack Migraine attacks may occur frequently for long periods in some patients. On the other hand, in some patients the migraine may remit for weeks, months or even years.

Migraine attacks may last for a period of four hours to several days if not treated. For some, the headaches associated with migraine attacks are mild and easily relieved with nonprescription analgesics. Quite often, migraine-related headaches are severe and temporarily disabling, especially when accompanied by nausea, vomiting, and discomfort from bright light.

A variety of abortive drugs are used for the acute treatment of migraine attacks. For example, one class of drugs that activate serotonin receptors (5-hydroxytryptamine agonists, or "5-HT agonists") mediate vasoconstriction and can abort migraine pain in about 70% of patients. The 5-HT agonist drug sumatriptan is available in oral, nasal spray and subcutaneous injection forms. Subcutaneous dosing is more effective but has greater potential adverse effects, which include flushing, nausea, esophageal constriction, and, rarely, coronary artery constriction. Other known 5-FIT agonists include eletriptan, naratriptan, rizatriptan and zolmitriptan. These oral agents may be less effective in the relief of acute migraine; however, the side effects of these agents are potentially less severe. The drug naratriptan is available in tablet form.

Ergot alkaloid derivatives, such as ergotamine tartrate and dihydroergotamine, in oral and parenteral preparations have been used as abortive drugs. Dopamine antagonist antiemetics, such as metoclopramide and prochlorperazine, may also be effective. It has been reported that analgesics should be used sparingly. They are effective in some patients but cause rebound headache with dose escalation in others. Rebound headache may be induced by repetitive and ongoing overuse of acute headache medication. Some nonsteroidal anti-inflammatory agents (NSAIDs) may be suitable for mild to moderate headaches. Opioids are generally avoided except under special circumstances and strict control.

Currently available abortive agents are often associated with recurrent migraine (triptans), rebound migraine (analgesics), or lack of sufficient efficacy when used with a convenient and practical method of administration (non-injected triptans). A need exists for a targeted prophylactic, acute, or subacute treatment of migraine that can substantially and reliably, with few or no side effects, diminish the likelihood of a patient being affected by disabling migraine symptoms during an important period of time and/or activity for that individual.

Some drugs taken every day may prevent migraine attacks from recurring. A beta-blocker, propranolol, provides long-term relief for about half the people who have frequent migraine-related headaches. The calcium channel blocker, verapamil, is effective for a few people. Recently, the antiseizure drug, divalproex, has been found to reduce the frequency of migraine-related headaches when taken daily. Methysergide is another preventive drug, but it must be taken intermittently because it can unpredictably cause a serious complication called retroperitoneal fibrosis, a formation of scar tissue deep within the abdomen, which can block blood supply to vital organs. Therefore, the use of this drug must be closely supervised by a medical provider.

Unfortunately, many patients experience significant side effects and/or lack of efficacy with the available and commonly prescribed prophylactic medications for migraine. A need exists for a prophylactic and/or targeted prophylactic treatment of migraine that uses active and effective agents or drugs with no or few complications or side effects.

SUMMARY OF THE INVENTION

The present invention provides a prophylactic or targeted prophylactic treatment of migraine that significantly reduces undesired risks or overcomes the problems of side effects associated with current methods of treatment, and that provides alternative methodologies for patients that cannot be treated or helped with current methods. Prophylactic or targeted prophylactic regimens are expected to be particularly relevant to the treatment of persons who have suffered a previous episode of, or are otherwise considered to be at increased risk of, migraine.

In one embodiment, the present invention provides a method for prophylactic treatment for migraine comprising regularly administering to a patient in need thereof a therapeutically effective amount of a combination comprising a cyclooxygenase-2 inhibitor and acetylsalicylic acid, or active derivative. Also, a prophylactic regimen using an alternate-day administration of a cyclooxygenase-2 inhibitor, and administration of acetylsalicylic acid or active derivative on days in which the cyclooxygenase-2 inhibitor is not administered, is effective in the prophylactic treatment of migraine. In this embodiment, the potential side effects of both medications or agents are reduced when used in combination or on alternate days.

In another embodiment, the invention provides a method for targeted prophylactic treatment of a migraine comprising: determining a time window or selected time period in which a patient desires to be free from migraine; and administering to the patient, at a time prior to the determined time window, a therapeutically effective amount of a cyclooxygenase-2 inhibitor, either alone or in combination with acetylsalicylic acid or active derivative, to prevent or reduce migraine symptoms during the time window.

In another embodiment, the invention provides a pharmaceutical composition to prophylactically treat migraine in unit dose form consisting essentially of a therapeutically effective combination of a cyclooxygenase-2 inhibitor, acetylsalicylic acid or derivative, and a pharmaceutically acceptable carrier.

Cyclooxygenase-2 inhibitors that that are suitable for use in the invention include known compounds that selectively inhibit cyclooxygenase-2 or that are obvious variants. One acceptable cyclooxygenase-2 inhibitor includes compounds represented by Formula I.

Formula I

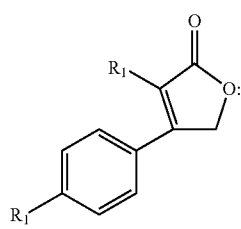

In Formula I, variable $R_1$ represents lower alkylsulfonyl or sulfamyl; and variable $R_2$ represents alkyl, cycloalkyl, aryl, mono-, di- or trisubstituted heteroaryl or benzoheteroaryl. A representative compound is rofecoxib.

Another acceptable cyclooxygenase-2 inhibitor includes compounds represented by Formula II.

Formula II

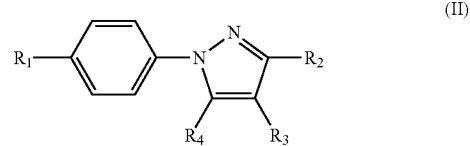

In Formula II, variable $R_1$ represents lower alkylsulfonyl or sulfamyl; variable $R_2$ represents alkyl, haloalkyl or halogen; variable $R_3$ represents hydrogen, lower alkyl or haloalkyl; and variable $R_4$ represents cycloalkyl, cycloalkenyl, aryl or substituted aryl. A representative compound is celecoxib.

Another acceptable cyclooxygenase-2 inhibitor includes compounds represented by Formula III.

Formula III:

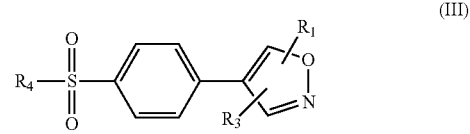

In Formula III, variable $R_1$ represents alkyl, carboxyalkyl, alkoxycarbonyl, aminocarbonyl, aminocarbonylalkyl, alkoxycarbonylalkyl, carboxyl, alkoxy, haloalkoxy, aralkoxy, heteroaralkoxy, cycloalkylalkoxy, alkylthio, aralkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, heterocyclo, heterocycloalkyl, aralkyl, halo, alkylamino, aralkylamino, N-alkyl-N-aralkylamino, heteroaralkylamino, N-alkyl-N-heteroaralkylamino, N-alkyl-N-cycloalkylalkylamino, arylcarbonyloxyalkyl, arylcarbonylthio, alkoxycarbonybxyalkyl alkylaminocarbonyloxyalkyl, alkoxycarbonylthioalkyl, or alkylaminocarbonylthioalkyl; variable $R_3$ represents cycloalkyl, cycloalkenyl, aryl or heterocyclo; wherein $R_3$ is optionally substituted at a substitutable position with one or more substituents independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and variable $R_4$ represents alkyl, hydroxyl, or amino.

DETAILED DESCRIPTION OF THE INVENTION

In one embodiment, the present invention provides a method for prophylactic treatment for migraine comprising regularly administering to a patient in need thereof a therapeutically effective amount of a combination comprising a cyclooxygenase-2 inhibitor and acetylsalicylic acid, or active derivative. This embodiment provides a method for long-term prophylactic treatment for migraine.

Prophylactic treatment is intended to reduce the frequency and intensity of migraine attacks. The prophylactic methods described herein do not necessarily result in complete freedom from symptoms associated with migraine attacks, but may provide for fewer symptoms or symptoms of reduced intensity. For many patients, it is the non-headache symptoms of migraine that are most disabling, and for which the patient is most desirous of relief. The prophylactic methods of the present invention are directed to the entire range of symptoms experienced by a patient during a migraine attack, and not merely at the prevention of headaches associated with a migraine attack.

The indications for preventative treatment of migraine have been published by the American Academy of Neurology. Prophylactic treatment is generally proposed for patients who suffer from two or more migraine attacks per month. Prophylactic treatment should also be considered for patients who experience less frequent migraine attacks that are more potent or even disabling. A third category of patients that may benefit from prophylactic treatment includes those who do not respond well to abortive treatments.

Cyclooxygenase-2 inhibitors ("Cox-2 inhibitors") are non-steroidal anti-inflammatory drugs ("NSAIDs") known for treatment of arthritis and other inflammatory conditions. Cox-2 inhibitors are commonly prescribed, owing to their lesser side effects as compared to other NSAIDs.

Cyclooxygenase enzymes have a role in the conversion of arachidonic acid to prostaglandins. A cyclooxygenase enzyme, cyclooxygenase-1, is known to be present in most tissues as a housekeeper enzyme that has homeostatic functions. Cyclooxygenase-1 plays a role in maintaining normal gastric mucosa and influences kidney function.

In the 1980s it was reported that cyclooxygenase enzyme level was increased in inflamed tissue. In the 1990s, it was discovered that the increase in cyclooxygenase enzyme associated with inflammation is due to what is now known as cyclooxygenase-2. Cyclooxygenase-2 is not present at basal conditions, but increases in response to inflammation including arthritis. Cyclooxygenase-2 is now understood to be responsible for converting arachidonic acid to 'inducible' prostaglandins, which produce inflammation and exacerbate tissue injury at the site of injury. On the other hand, production of 'good' constitutive prostaglandins is facilitated by cyclooxygenase-1.

Since cyclooxygenase-1 plays a role in regulating normal body functions, inhibition of cyclooxygenase-1 is usually undesirable. Furthermore, cyclooxygenase-1 is present in platelets, and inhibition of cyclooxygenase-1 interferes with normal platelet aggregation. This "anti-platelet effect" is thought to be due to an inhibition of the production of thromboxane. The anti-platelet effect can sometimes provide a benefit for the treatment of certain conditions, such as in cardiovascular prophylaxis.

The inhibition of cyclooxygenase-2, on the other-hand, is desirable for reducing the level of inducible prostaglandins associated with inflammation. Inhibition of cyclooxygenase-2 is furthermore not known to interfere with platelet aggregation, since cyclooxygenase-2 is not normally present in platelets. Cyclooxygenase-2 and cyclooxygenase-1 are about 60% homologous.

Non-selective NSAIDs are now known to inhibit prostaglandin formation by both cyclooxygenase-1 and cyclooxygenase-2. The non-selectivity has become associated with undesirable side effects. Inhibition of cyclooxygenase-1 is thought to result in gastrointestinal, renal, and platelet complications. Therefore, cyclooxygenase-2 inhibitors have been developed to preferentially inhibit only the cyclooxygenase-2 enzyme without undue inhibition of cyclooxygenase-1. The Cox-2 inhibitors are designed to work as effectively as non-selective NSAIDs in relieving pain due to inflammation, but with fewer side effects associated with non-selective NSAIDs including ulcers and gastrointestinal bleeding.

Compounds that are cyclooxygenase-2 inhibitors and methods for the preparation of these compounds have been reported in the art. See, for example, U.S. Pat. Nos. 5,380,738; 5,344,991; 5,393,790; 5,466,823; 5,434,178; 5,474,995; 5,510,368; 5,521,207, 5,563,165, 5,604,260, 5,633,272, 5,691,374, 5,760,068, 5,859,257, 6,239,173, and 6,248,745; and international applications WO96/06840, WO96/03388, WO96/03387, WO95/15316, WO94/15932, WO94/27980, WO95/00501, WO94/13635, WO94/20480 and WO94/26731. Representative compounds that are commercially available include rofecoxib (4-[4-(methylsulfonyl)phenyl]-3-phenyl-2(5H)-furanone), marketed under the trade name VIOXX (Merck & Co., Inc., Whitehouse Station, N.J.), celecoxib (4-[5-(4-methylphenyl)-3-(trifluoromethyl)-1H-pyrazol-1-yl]), marketed under the trade name CELEBREX (G.D. Searle & Co., Chicago, Ill.), and valdecoxib (4-(5-methyl-3-phenyl-4-isoxazolyl)benzenesulfonamide), marketed under the trade name BEXTRA ((G.D. Searle & Co.)

The term "cyclooxygenase-2 inhibitor" (or "Cox-2 inhibitor") includes compounds that selectively inhibit cyclooxygenase-2 over cyclooxygenase-1 ("Cox-1"). Inhibition is often stated as an $IC_{50}$ value. The term "$IC_{50}$" refers to the concentration of the compound that is required to produce 50% inhibition of cyclooxygenase activity. Preferably, the cyclooxygenase-2 inhibitor compounds have a cyclooxygenase-2 $IC_{50}$ value of less than about 0.5 µM, and also have a selectivity ratio of cyclooxygenase-1 inhibition over cyclooxygenase-2 inhibition of at least 50, and more preferably at least 100. Preferably, the compounds have a cyclooxygenase-1 $IC_{50}$ of greater than about 1 µM, and more preferably greater than 20 µM. The selectivity observed for cyclooxygenase-2 inhibitors may indicate an ability to reduce the incidence of common NSAID-induced side effects when used.

For some patients, the methods and compositions described herein may be more effective, and associated with fewer or reduced side effects, if a highly-selective cyclooxygenase-2 inhibitor is employed, such as rofecoxib or valdecoxib, which are thought to be significantly more selective for cyclooxygenase-2 inhibition than other known selective cyclooxygenase-2 inhibitors such as celecoxib.

Suitable classes of compounds that inhibit cyclooxygenase-2 includes compounds represented by Formulas I-III, or pharmaceutically acceptable salts thereof that are similarly inhibitors of cyclooxygenase-2. Suitable embodiments of cyclooxygenase-2 inhibitors are represented by Formula I.

Formula I

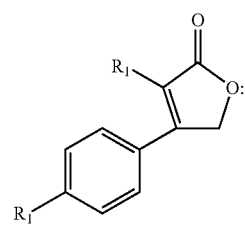

wherein:
$R_1$ is lower alkylsulfonyl or sulfamyl; and
$R_2$ is alkyl, cycloalkyl, aryl, mono-, di- or trisubstituted heteroaryl or benzoheteroaryl.

Suitable embodiments further include compounds represented by Formula I wherein $R_1$ is lower alkylsulfonyl; and $R_2$ is mono- or disubstituted phenyl.

Still other embodiments of cyclooxygenase-2 inhibitors are compounds represented by Formula II.

Formula II

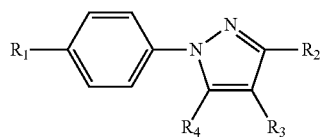

(II)

wherein:
$R_1$ is lower alkylsulfonyl or sulfamyl;
$R_2$ is alkyl, haloalkyl or halogen;
$R_3$ is hydrogen, lower alkyl or haloalkyl; and
$R_4$ is cycloalkyl, cycloalkenyl, aryl or substituted aryl.

Further embodiments include compounds represented by Formula II wherein $R_1$ is sulfamyl; $R_2$ is haloalkyl; $R_3$ is hydrogen or lower alkyl; and $R_4$ is aryl or substituted aryl.

Other embodiments include cyclooxygenase-2 inhibitors represented by Formula III.

Formula III:

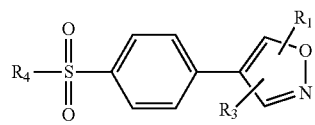

(III)

wherein:
$R_1$ is alkyl, carboxyalkyl, alkoxycarbonyl, aminocarbonyl, aminocarbonylalkyl, alkoxycarbonylalkyl, carboxyl, alkoxy, haloalkoxy, aralkoxy, heteroaralkoxy, cycloalkylalkoxy, alkylthio, aralkylthio, heteroaralkylthio, cycloalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, heterocyclo, heterocycloalkyl, aralkyl, halo, alkylamino, aralkylamino, heteroaralkylamino, N-alkyl-N-heteroaralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, or alkylaminocathonylthioalkyl;
$R_3$ is cycloalkyl, cycloalkenyl, aryl or heterocyclo; and
$R_4$ is alkyl, hydroxyl, or amino.

Further embodiments include compounds of Formula III wherein $R_3$ is optionally substituted at a substitutable position with one or more substituents independently selected from alkyl, cyano, carboxyl, alkoxycarbonyl, haloalkyl, hydroxyl, hydroxyalkyl, haloalkoxy, amino, alkylamino, acylamino, aminoalkyl, nitro, alkoxyalkyl, alkylsulfinyl, alkylsulfonyl, aminosulfonyl, halo, alkoxy and alkylthio. In a preferred embodiment of a compound of Formula III, $R_1$ is methyl, $R_3$ is phenyl, and $R_4$ is amino.

The terms that are used in the formulas have the following definitions:

The term "hydrogen" means a single hydrogen substituent (H).

The term "hydroxy" or "hydroxyl" means an —OH substituent.

The term "amino" means an —NH$_2$ substituent, or a substituted amino group having substituents that are bonded to a saturated nitrogen by single bonds (such as, e.g., alkylamino or arylamino).

The term "cyano" means a —CN substituent.

The term "halo" means halogen substituents such as fluorine, chlorine, bromine or iodine substituents.

The term "alkyl" means linear or branched saturated hydrocarbon substituents having one to about twenty carbon atoms or, preferably, one to about twelve carbon atoms. Some alkyl substituents are "lower alkyl" substituents having one to about ten carbon atoms. Others are lower alkyl substituents having one to about six carbon atoms. Examples of such substituents include methyl, ethyl, n-propyl, isopropyl, n-butyl, isobutyl, sec-butyl, tert-butyl, pentyl, iso-amyl, and hexyl. The term "alkyl" takes the same meaning when used within the definition of other substituents herein, such as "haloalkyl," "alkylsulfonyl," "alkoxyalkyl" and "hydroxyalkyl."

The term "cycloalkyl," means saturated carbocyclic substituents having three to twelve carbon atoms. Some cycloalkyl substituents are lower cycloalkyl substituents having three to about eight carbon atoms. Examples of such substituents include cyclopropyl, cyclobutyl, cyclopentyl and cyclohexyl.

The term "cycloalkylalkyl" embraces cycloalkyl-substituted alkyl substituents such as cyclohexylmethyl, cyclopentylethyl, cyclopentylmethyl, cyclohexylethyl, and cyclobutylpropyl.

The term "cycloalkenyl" means partially unsaturated carbocyclic substituents having three to twelve carbon atoms. Some cycloalkenyl substituents are "lower cycloalkenyl" substituents having four to about eight carbon atoms. Examples of such substituents include cyclobutenyl, cyclopentenyl, cyclopentadienyl, and cyclohexenyl.

The terms "hydroxyalkyl" and "hydroxylalkyl" embrace linear or branched alkyl substituents having one to about ten carbon atoms any one of which may be substituted with one or more hydroxyl substituents. More preferred hydroxyalkyl substituents are "lower hydroxyalkyl" substituents having one to six carbon atoms and one or more hydroxyl substituents. Examples of such substituents include hydroxymethyl, hydroxyethyl, hydroxypropyl, hydroxybutyl and hydroxyhexyl.

The term "haloalkyl" means alkyl substituents wherein any one or more of the alkyl hydrogens is substituted with a halogen substituent as defined above; the haloalkyl may be monohaloalkyl, dihaloalkyl or polyhaloalkyl. A monohaloalkyl substituent, for example, may have an iodine, bromine, chlorine or fluorine atom within the substituent. Dihalo and polyhaloalkyl substituents may have two or more of the same halogen substituents or a combination of different halogen substituents. Examples of haloalkyl substituents include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The terms "alkoxy" and "alkyloxy" mean linear or branched oxygen-containing substituents having an alkyl portions of one to about ten carbon atoms linked directly to the oxygen. Some alkoxy substituents are "lower alkoxy" substituents having one to six carbon atoms. Examples of such substituents include methoxy, ethoxy, propoxy, butoxy and tert-butoxy. The alkoxy substituents may be further substituted with one or more halogen substituents such as fluorine, chlorine or bromine substituents to provide haloalkoxy substituents. Some haloalkoxy substituents are lower haloalkoxy substituents having one to six carbon atoms and one or more halogen substituents. Examples of such substituents include fluoromethoxy, chloromethoxy, trifluoromethoxy, trifluoroethoxy, fluoroethoxy and fluoropropoxy.

The term "alkoxyalkyl" means alkyl substituents having one or more alkoxy substituents attached to the alkyl substituent, that is, to form monoalkoxyalkyl and dialkoxyalkyl substituents. An alkoxyalkyl further including a cycloalkyl substituent is a "cycloalkylalkoxy" substituent.

The term "aryl" means a carbocyclic aromatic substituent containing one, two or three rings where these rings may be attached together in a pendent manner or may be fused. For example, the term "aryl" includes aromatic substituents such as phenyl, naphthyl, tetrahydronaphthyl, indane and biphenyl. Aryl substituents within this definition may also be substituted at a substitutable position with one or more substituents selected independently from alkyl, haloalkyl, alkoxyalkyl, alkylaminoalkyl, carboxyalkyl, alkoxycarbonylalkyl, aminocarbonylalkyl, alkoxy, arylalkoxy, hydroxyl, amino, halo, nitro, alkylamino, acyl, cyano, carboxy, aminocarbonyl, thioalkyl, alkoxycarbonyl and arylalkoxycarbonyl.

The term "aralkyl" embraces aryl-substituted alkyl substituents such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable.

The term "aralkoxy" embraces aralkyl substituents attached through an oxygen atom to other substituents.

The term "aralkoxyalkyl" embraces aralkoxy substituents attached through an oxygen atom to an alkyl substituent.

The term "aryloxyalkyl" embraces substituents having an aryl substituents attached to an alkyl substituent through a divalent oxygen atom.

The term "heteroaryl" means unsaturated or saturated, unsubstituted or substituted heterocyclic substituents; i.e., cyclic substituents having both carbon atoms and heteroatoms (such as nitrogen, oxygen, or sulfur, for example) as ring members.

The term "heteroaralkyl" embraces heteroaryl-substituted alkyl substituents, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy.

The term "heterocycloalkyl" embraces heterocyclo-substituted alkyl substituents, such as pyrrolidinylmethyl, piperazinylmethyl, piperidinylmethyl, furanylethyl, tetrahydrofurylethyl and heteroaralkyl substituents.

The term "heteroaralkoxy" embraces heteroaralkyl substituents attached through an oxygen atom to other substituents.

The term "benzoheteroaryl" means a substituent comprising a heteroaryl ring fused to a benzene ring.

The terms "carboxy" or "carboxyl," whether used alone or with other terms, such as "carboxyalkyl," denotes —C(O)OH.

The term "acyl" denotes a substituent provided by the residue after removal from an organic acid group of the terminal hydroxyl.

The term "carboxyalkyl" means alkyl substituents substituted with a carboxy substituent.

The terms "alkylcarbonyl", "arylcarbonyl" and "aralkylcarbonyl" include substituents having alkyl, aryl and aralkyl substituents, as defined above, attached via an oxygen atom to a carbonyl substituent (i.e., —C(O)—). Examples of such substituents include substituted or unsubstituted methylcarbonyl, ethylcarbonyl, phenylcarbonyl and benzylcarbonyl.

The term "alkoxycarbonyl" means a substituent containing an alkoxy substituent attached via an oxygen atom to a carbonyl substituent. Examples of such "alkoxycarbonyl" ester substituents include substituted or unsubstituted methoxycarbonyl, ethoxycarbonyl, propoxycarbonyl, butoxycarbonyl and hexyloxycarbonyl.

The term "alkoxycarbonylalkyl" means a substituent containing an alkoxycarbonyl substituent, as defined above, attached to an alkyl substituent. Examples of such "alkoxycarbonylalkyl" ester substituents include substituted or unsubstituted methoxycarbonylmethyl, butoxycarbonylmethyl and hexyloxycarbonylethyl.

The term "alkoxycarbonyloxyalkyl" means a substituent containing an alkoxycarbonyl substituent, as defined above, substituting for a hydrogen on an oxyalkyl substituent.

The term "aminoalkyl" embraces alkyl substituents substituted with amino substituents.

The term "alkylamino" denotes amino groups which have been substituted with one or two alkyl substituents. Suitable "alkylamino" may be mono or dialkylamino such as N-methylamino, N-ethylamino, N,N-dimethylamino, N,N-diethylamino or the like.

The term "alkylaminoalkyl" means an alkyl substituent having one or more alkyl hydrogen substituted with an aminoalkyl substituent.

The term "cycloalkylamino" denotes amino groups which have been substituted with one or two cycloalkyl substituents, as defined above.

The term "arylamino" denotes amino groups which have been substituted with one or two aryl substituents, such as N-phenylamino. The "arylamino" substituents may be further substituted on the aryl ring portion of the substituent.

The term "aralkylamino" embraces aralkyl substituents attached through an nitrogen atom to other substituents.

The term "heteroaralkylamino" embraces heteroaralkyl substituents, as defined above, attached through an nitrogen atom to other substituents.

The term "aminocarbonyl" denotes an amide group of the formula —C(=O)NH$_2$.

The term "aminocarbonylalkyl" denotes an alkyl substituent having one or more aminocarbonyl substituent attached to the alkyl substituent.

The term "alkylcarbonylaminoalkyl" embraces substituents having one or more alkyl substituents attached to a carbonyl substituent further attached to an aminoalkyl substituent.

The term "alkylaminocarbonyloxyalkyl" embraces substituents having an aminoalkyl substituent attached to a carbonyl substituent further attached to an oxyalkyl substituent.

The term "alkylthio" means substituents containing a linear or branched alkyl substituent of one to about ten carbon atoms attached to a divalent sulfur atom. Some alkylthio substituents are "lower alkylthio" substituents having alkyl substituents of one to six carbon atoms. Examples of such lower alkylthio substituents are methylthio, ethylthio, propylthio, butylthio and hexylthio.

The term "alkylthioalkyl" embraces substituents containing an alkylthio substituent attached through the divalent sulfur atom to an alkyl substituent of one to about ten carbon atoms. More preferred alkylthioalkyl substituents are "lower alkylthioalkyl" substituents having alkyl substituents of one to six carbon atoms. Examples of such lower alkylthioalkyl substituents include methylthiomethyl.

The term "cycloalkylalkylthio" embraces substituents having cycloalkyl substituents, as defined above, attached to an alkylthio substituent. More preferred cycloalkylthio substituents are "lower cycloalkylalkylthio" substituents having cycloalkyl substituents of three to six carbon atoms.

The term "aralkylthio" embraces aralkyl substituents attached to a sulfur atom.

The term "aralkylthioalkyl" embraces aralkylthio substituents attached through a sulfur atom to an alkyl substituent.

The term "heteroaralkylthio" embraces heteroaralkyl substituents attached through a sulfur atom to other substituents.

The term "arylthioalkyl" embraces substituents having an aryl substituents attached to an alkyl substituent through a divalent sulfur atom.

The term "sulfonyl", whether used alone or linked to other terms such as alkylsulfonyl, denotes respectively divalent substituents $-S(=O)_2-$.

The term "alkylsulfonyl" embraces substituents containing a linear or branched alkyl substituent, of one to ten carbon atoms, attached to a divalent $-S(=O)_2-$ substituent. The term "lower alkylsulfonyl" means $-SO_2$-alkyl substituents wherein the alkyl group has one to six carbon atoms. Examples of such lower alkylsulfonyl substituents include methylsulfonyl, ethylsulfonyl and propylsulfonyl. The alkylsulfonyl substituents may be further substituted with one or more halogen substituents such as fluorine, chlorine or bromine substituents atoms to provide haloalkylsulfonyl substituents.

The terms "sulfamyl," "aminosulfonyl," and "sulfonamidyl," denotes the substituent $-S(O_2)NH_2$.

The phrase "pharmaceutically acceptable salts" means salts commonly used to form alkali metal salts and to form addition salts of free acids or free bases. The nature of the salt is not critical, provided that it is pharmaceutically acceptable. Suitable pharmaceutically acceptable acid addition salts of compounds of Formulas I-III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, heterocyclyl, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically acceptable base addition salts of compounds of Formulas I-III include metallic salts made from aluminum, calcium, lithium, magnesium, potassium, sodium and zinc or organic salts made from N,N-dibenzylethylenediamine, chloroprocaine, choline, diethanolamine, ethylenediamine, meglumine (N-methylglucamine) and procaine. All of these salts may be prepared by conventional means from the corresponding compounds of Formulas I-III by reacting, for example, the appropriate acid or base with the compounds of Formulas I-III.

Acetylsalicylic acid, commonly known as "aspirin," is a non-selective NSAID. Acetylsalicylic acid, unlike many other NSAIDs, irreversibly inhibits a cyclooxygenase enzyme by forming an enzyme-inhibitor complex after a covalent conformational change in the enzyme. Acetylation of cyclooxygenase-1 by aspirin is an irreversible process that inhibits the enzyme's cyclooxygenase activity (i.e., oxygenation of arachidonic acid) but not its peroxidase activity (i.e., subsequent reduction of the oxygenated arachidonic acid to prostaglandin). Aspirin is well-known to have an antiplatelet effect, and is commonly administered as a preventative for cardiovascular diseases. The antiplatelet effect of acetylsalicylic acid is long-lasting, since the inhibition of cyclooxygenase-1 is irreversible. In contrast, the antiplatelet effect for other NSAIDs diminishes over time, since their inhibition of cyclooxygenase-1 is reversible.

Acetylsalicylic acid or any of its active derivatives are useful in the methods and compositions of the present invention. By "active derivative" it is meant an acetylsalicylic acid derivative that is active in inhibiting cyclooxygenase-1 and/or cyclooxygenase-2, particularly a derivative that can by hydrolyzed to form, or can otherwise release, salicylate in vivo. Active derivatives may include salts such as sodium, magnesium, or bismuth salts of salicylic acid, for example. Active derivatives may also include functional derivatives such as choline salicylate or choline magnesium trisalicylate.

The method for prophylactic treatment includes regular administration of a therapeutically effective amount of a combination comprising a cyclooxygenase-2 inhibitor and acetylsalicylic acid or active derivative. Administration of the combination including a cyclooxygenase-2 inhibitor may include administration of one or more cyclooxygenase-2 inhibitors.

Administration of the combination is intended to include co-administration of each agent (i.e., the cyclooxygenase-2 inhibitor and the acetylsalicylic acid or active derivative) in a sequential manner in a regimen that will provide beneficial effects of the drug combination. Administration of the combination is intended as well to include co-administration of these agents in a substantially simultaneous manner, such as in a single capsule or other dosage unit having a fixed ratio of these active agents, or in multiple, separate capsules for each agent. The term "co-administration" indicates that the cyclooxygenase-2 inhibitor and acetylsalicylic acid or active derivative are administered as part of a planned course of treatment for preventing migraine.

The combination is administered regularly, meaning that the combination is administered periodically or aperiodically over a period of several days or weeks, in an effort to prevent migraine attacks, and is not merely administered in response or reaction to migraine symptoms. Regular administration may include once-daily administration of each agent, administration on alternate days, or any other periodic or aperiodic schedule that is determined to be effective as a planned course of treatment for preventing migraine.

The phrase "therapeutically effective" is intended to qualify the amount of each active agent or compound for use in a combination therapy which will achieve the goal of improvement in migraine treatment or therapy or reduced frequency or incidence of migraine, while avoiding adverse side effects typically associated with alternative therapies.

For appropriate therapeutic indications, the dosage administered will vary with the compound employed, the mode of administration and the treatment desired. However, in general, satisfactory results are obtained when the solid form of the compounds are administered at a daily dosage of between 1 milligram and 2000 milligrams per day.

A unit dose of about 0.01 to 100 milligrams/kg body weight, preferably between about 0.1 and about 50 milligrams/kg body weight and most preferably from about 1 to 20 milligrams/kg body weight, may be appropriate.

The amount of the compound actually administered will be determined by a physician in light of the relevant circumstances including the condition to be treated, the choice of compound to be administered, the age, weight, and response symptoms, and the chosen route of administration. Therefore the dosage ranges are not intended as a limitation to the scope of the invention.

By way of example only, the combination may include about 12.5 to about 50 milligrams rofecoxib per day, or about 12.5 to about 25 milligrams rofecoxib per day. Alternatively, the combination may include about 200 to about 400 milligrams celecoxib per day, or about 10 to about 20 milligrams valdecoxib per day. The combination may include about 50 to about 325 milligrams acetylsalicylic acid or salicylate salt per day.

The active agents or compounds of this invention may be used separately, or preferably as a pharmaceutical composition in which the compounds or derivatives are in admixture with a pharmaceutically acceptable adjuvant, diluent or carrier in a form appropriate for enteral or parenteral administration. The pharmaceutical composition preferably comprises less than 80% and more preferably less than 50% of the agent, compound or derivative. Examples of suitable adjuvants, diluents and carriers are well known and include microcrystalline cellulose, calcium phosphate, diatomaceous earth, a sugar such as lactose, dextrose or mannitol, talc, stearic acid, starch, sodium bicarbonate and/or gelatin.

Also, a prophylactic regimen using a regular alternate-day administration of a cyclooxygenase-2 inhibitor, and administration of acetylsalicylic acid or active derivative on days in which the cyclooxygenase-2 inhibitor is not administered, is effective in the prophylactic treatment of migraine. In this embodiment, the potential side effects of both medications or agents are reduced when used in combination on alternate days. By way of example only, about 12.5 to about 25 milligrams rofecoxib may be administered every-other-day, and about 325 milligrams acetylsalicylic acid or salicylate salt may be administered on days in which rofecoxib is not administered.

In another embodiment, the invention provides a method for targeted prophylactic treatment of a migraine condition. The method includes determining a time window or selected time period in which a patient desires to be free from migraine; and administering to the patient, at a time prior to the determined time window, a therapeutically effective amount of a cyclooxygenase-2 inhibitor, either alone or in combination with acetylsalicylic acid or active derivative, to prevent or reduce migraine symptoms during the time window.

Targeted prophylactic treatment is intended to either prevent, or reduce the intensity of, one or more migraine attacks. The targeted prophylactic methods described herein do not necessarily result in complete freedom from symptoms associated with a migraine attack, but may provide for fewer symptoms or symptoms of reduced intensity. For many patients, it is the non-headache symptoms of migraine that are most disabling, and for which the patient is most desirous of relief. The targeted prophylactic methods of the present invention are directed to the entire range of symptoms experienced by a patient during a migraine attack, and not merely at the prevention of headaches associated with a migraine attack.

The "targeted prophylactic" approach is relevant for persons with frequent, recurring migraine symptoms who anticipate critical activities during which it is very important to prevent or minimize their migraine-related symptoms. Furthermore, the targeted prophylactic approach may be especially relevant for persons who expect to experience a stimulus that is known to trigger migraine symptoms or is associated with an increased chance of experiencing migraine symptoms. By way of example, such stimuli include stress, hormonal spikes (such as during regular or irregular menstrual cycles), glare (such as when driving, skiing, flying or boating on a clear day), etc.

The time window would include the period of time over which the patient anticipates participating in the critical activities during which the patient desires to be as free from migraine symptoms as is possible, or the period over which a patient expects to experience a migraine-triggering stimulus. The time window or selected time period could also include a period (lasting hours or several days) after a known or probable migraine-inducing stimulus, such as the consumption of red wine, disruption of sleep, or a skipped meal.

For some of these patients, it is possible that early or premonitory migraine symptoms will be evident at the time of administration of the agent or agents to be used for treatment, but the administration will still take place prior to the critical activities or expected stimulus. In this case, the treatment may be termed "acutely targeted" if the goal is to eliminate or substantially reduce the migraine symptoms during the particular time or activity for the patient. Often, the patient will learn to recognize early or premonitory migraine symptoms, or will be aware of a pattern or frequency of migraine attacks, and will be able to self-administer the treatment at an appropriate time.

In other cases, there will be no early or premonitory symptoms of migraine when this agent or agents are administered for targeted prophylaxis. This dosing strategy is very useful for those persons with frequent, recurring stimuli or high-demand activities that are associated with frequent migraine symptoms. Again, the patient may be able to self-administer at an appropriate time, when the patient anticipates participating in a critical activity or the patient expects to experience a migraine-triggering stimulus.

Prior to the determined time window, a therapeutically effective amount of a cyclooxygenase-2 inhibitor is administered to the patient. By "prior," it is meant that the administration is temporally before the determined time window, but sufficiently close in time so that the prophylactic effect of the cyclooxygenase-2 inhibitor is experienced throughout most or all of the determined time window.

The patient is administered a therapeutically effective amount of a cyclooxygenase-2 inhibitor, either alone or in combination with acetylsalicylic acid or active derivative.

By "alone," it is meant that the cyclooxygenase-2 inhibitor is administered without any other pharmaceutically active agent that is intended to prophylactically treat a migraine condition. In an embodiment where the cyclooxygenase-2 inhibitor is administered alone, the method for prophylactic treatment consists essentially of administration of a therapeutically effective amount of the cyclooxygenase-2 inhibitor.

In an embodiment where a combination of a cyclooxygenase-2 inhibitor and acetylsalicylic acid or derivative is administered, the step of administering is intended to include co-administration of each agent (i.e., the cyclooxygenase-2 inhibitor and the acetylsalicylic acid or active derivative) in a sequential manner in a regimen that will provide beneficial effects of the drug combination during the determined time window. Administration of the combination is intended as well to include co-administration of these agents in a substantially simultaneous manner, such as in a single capsule or other dosage unit having a fixed ratio of these active agents, or in multiple, separate capsules for each agent. The term "co-administration" indicates that the cyclooxygenase-2 inhibitor and acetylsalicylic acid or active derivative are administered as part of the targeted prophylactic treatment for preventing migraine.

For the targeted prophylactic method, the phrase "therapeutically effective" is intended to qualify the amount of an active agent or compound, alone or in combination, for use in the targeted prophylactic therapy which will achieve the goal of reducing or preventing migraine symptoms during the determined time window.

By way of example only, about 12.5 to about 50 milligrams rofecoxib may be administered. Alternatively, about 200 to about 400 milligrams celecoxib may be administered; or about 10 to about 20 milligrams valdecoxib may be administered. In combination, the administration may include about 50 to about 325 milligrams acetylsalicylic acid or salicylate salt.

In another embodiment, the invention provides a pharmaceutical composition in unit dose form useful for prophylactic treatment of migraine, consisting essentially of a therapeutically effective combination of a cyclooxygenase-2 inhibitor, acetylsalicylic acid or active derivative, and a pharmaceutically acceptable carrier. Although particularly useful for prophylactic treatment of migraine, the pharmaceutical composition may also be suitable for other inflammatory conditions.

The pharmaceutical compositions include or consist essentially of the active agents or compounds of this combination therapy in association with one or more non-toxic, pharmaceutically acceptable carriers, diluents, or adjuvants (collectively referred to as "carrier" materials). Aside from a cyclooxygenase-2 inhibitor and acetylsalicylic acid or active derivative, the pharmaceutical composition generally will not include any other pharmaceutically active agent intended for, and effective in, prophylactic treatment of migraine.

The composition may be suitable for administration orally, intravascularly, intraperitoneally, subcutaneously, intramuscularly, intranasally, or topically, for example. Alternatively, the composition may be suitable for use with a device that provides local or systemic controlled release of the active agents.

The pharmaceutical composition preferably contains a dose of each active agent in an amount effective for the prophylactic treatment for which it is intended. By way of example, a pharmaceutical composition may be intended for prophylactic treatment by regular administration, or may be intended for targeted prophylactic treatment by one-time administration. In each case, the pharmaceutical composition may contain quantities of active agents tailored for the specific application.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition where, for example, saline, dextrose or water may be used as a suitable carrier. For therapeutic purposes, the active compounds of this combination invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxy-propylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

By way of example only, the composition may include about 12.5 to about 50 milligrams rofecoxib. Alternatively, the composition may include about 200 to about 400 milligrams celecoxib, or about 10 to about 20 milligrams valdecoxib. The composition may include about 50 to about 325 milligrams acetylsalicylic acid or salicylate salt. In one embodiment, the composition includes about 200 milligrams celecoxib and about 325 milligrams acetylsalicylic acid or salicylate salt.

The following examples further describe the method of the present invention. These examples illustrate alternative embodiments of the invention and do not limit the scope of the appended claims.

EXAMPLES

Example 1

A patient with an established history of recurrent migraine was treated with a daily oral dose of 25 milligrams of VIOXX (rofecoxib tablets, Merck & Co, Inc., Whitehouse Station, N.J.). The patient was free of migraine symptoms during the first week of use and noticed a reduced intensity of the symptoms of subsequent migraine attacks as well as a reduced frequency of migraine attacks during the treatment period of three to four weeks while taking the VIOXX tablets.

Example 2

A patient with an established history of recurrent migraine was treated with a daily oral dose of 25 milligrams of VIOXX (rofecoxib tablets, Merck) and 325 milligrams of enteric aspirin tablets (over-the-counter buffered aspirin). The patient noted a lower incidence and intensity of migraine symptoms while taking the combination of VIOXX and aspirin tablets.

Example 3

A patient with an established history of recurrent migraine was treated with a daily oral dose of 12.5 milligrams of VIOXX (rofecoxib tablets, Merck & Co, Inc., Whitehouse Station, N.J.) and 162.5 milligrams aspirin (over-the-counter aspirin tablets) for about four weeks. Then the patient switched to an every-other-day regimen of 12.5-25 milligrams VIOXX tablets alternating with 325 milligrams aspirin tablets. The patient noted a lower incidence and intensity of migraine symptoms during the treatment period of about 52 weeks. He also noted a significant reduction in the use of 5-HT receptor agonists (IMITREX injections and nasal spray, Glaxo Wellcome Inc., Research Triangle Park, N.C.; and AMERGE tablets, Glaxo Wellcome) while taking the combination of VIOXX and aspirin tablets.

Example 4

A patient with an established history of recurrent migraine was treated with a daily oral dose of 200 milligrams of CELE- BREX (celecoxib capsules, G.D. Searle & Co., Chicago, Ill.). The patient was free of migraine symptoms during the treatment period of ten to fourteen days and noticed a reduced intensity of the symptoms of a subsequent migraine while taking the CELEBREX capsules.

Example 5

A patient with an established history of migraine brought on by glare associated with an ophthalmic operating room microscope was treated with 6 milligrams of IMITREX by injection (Glaxo Wellcome Inc.), and an oral dose of 12.5 to 25 milligrams of VIOXX (Merck & Co, Inc.) the night before a scheduled ophthalmic operation. The patient was free of migraine symptoms before, during and after the scheduled operation after targeted prophylactic treatment with the combination of IMITREX injection and VIOXX tablet treatment on many occasions.

On other occasions the patient experienced migraine symptoms at a greatly reduced intensity as compared to a full-fledged migraine, so that he was able to function effectively during the scheduled operations.

Example 6

A patient with an established history of migraine brought on by glare associated with repeated use of a slit lamp biomicroscope was treated with an oral dose of 12.5 to 25 milligrams of VIOXX (Merck & Co, Inc.) the night before a scheduled clinic. The patient was free of migraine symptoms before, during and after the scheduled clinic after targeted prophylactic treatment with VIOXX.

Example 7

A patient with an established history of migraine brought on by glare associated with repeated use of a slit lamp biomicroscope was treated with an oral dose of 12.5 to 25 milligrams of VIOXX (Merck & Co, Inc.) and 325 milligrams aspirin (over-the-counter aspirin tablets) the night before a scheduled clinic. The patient was free of migraine symptoms before, during and after the scheduled clinic after targeted prophylactic treatment with the combination of VIOXX and aspirin.

Example 8

A patient with an established history of migraine brought on by occasional consumption of red wine (as a beverage or in a sauce or dressing) was treated with an oral dose of 12.5 to 25 milligrams of VIOXX (Merck & Co, Inc.) on the same day as such consumption before migraine attack symptoms are evident. The patient was either free of, or experienced substantially reduced, migraine symptoms for a time period during which symptoms would normally be experienced or expected in absence of treatment with VIOXX.

On some such occasions, the patient was further treated with daily oral doses of 12.5 to 25 milligrams VIOXX subsequent to the consumption of red wine. The patient noted that the therapeutic benefit extended for several days following the consumption of red wine.

Example 9

A patient with an established history of migraine brought on by occasional consumption of red wine (as a beverage or in a sauce or dressing) was treated with an oral dose of 12.5 to 25 milligrams of VIOXX (Merck & Co, Inc.) and 162.5 milligrams aspirin (over-the-counter aspirin tablets) on the same day as such consumption before migraine attack symptoms are evident. The patient was either free of, or experienced substantially reduced, migraine symptoms for a time period during which symptoms would normally be experienced or expected in absence of treatment with a combination of VIOXX and aspirin.

On some such occasions, the patient was further treated with daily oral doses of 12.5 to 25 milligrams VIOXX and 162.5 milligrams aspirin subsequent to the consumption of red wine. The patient noted that the therapeutic benefit extended for several days following the consumption of red wine.

On other such occasions, the patient was further treated with every-other-day oral doses of 12.5 to 25 milligrams VIOXX, and alternate-day doses of 162.5 milligrams aspirin, subsequent to the consumption of red wine. The patient noted that the therapeutic benefit extended for several days following the consumption of red wine.

Example 10

A patient with a well-established history of recurrent migraine attacks learns to recognize his prodromal symptoms of altered mood, irritability, fatigue, and craving for sweets which typically occur 3 to 24 hours prior to the fully developed phase of his migraine. He learns over time that these prodromal symptoms eventually lead to a migraine attack in most cases. His migraine attacks typically include unusual sensitivity to light and sound, difficulty concentrating, headache, and less commonly, nausea. As soon as he recognizes the prodromal symptoms, he takes a one-time dose of 25-50 milligrams of rofecoxib, followed by 12.5-25 milligrams of rofecoxib daily. He notes that he is either free of, or has greatly reduced, migraine attack symptoms subsequent to taking the rofecoxib. Continued daily dosing extends that period of benefit for several days (or longer) subsequent to the initial symptoms.

Example 11

A patient with a well-established history of recurrent migraine attacks learns to recognize his prodromal symptoms of altered mood, irritability, fatigue, and craving for sweets which typically occur 3 to 24 hours prior to the fully developed phase of his migraine. He learns over time that these prodromal symptoms eventually lead to a migraine attack in most cases. His migraine attacks typically include unusual sensitivity to light and sound, difficulty concentrating, headache, and less commonly, nausea. As soon as he recognizes the prodromal symptoms, he takes a one-time dose of 25-50 milligrams of rofecoxib and 162.5-325 milligrams aspirin, followed by 12.5-25 milligrams of rofecoxib and 162.5-325 milligrams aspirin daily. He notes that he is either free of or has greatly reduced migraine attack symptoms subsequent to taking the rofecoxib. Continued daily dosing extends that period of benefit for several days (or longer) subsequent to the initial symptoms.

Example 12

A 45-year-old female patient with a well-established history of recurrent migraine attacks heralded by an aura of dysphasia (i.e., difficulty in finding words) begins taking 25-50 milligrams of rofecoxib at the onset of the dysphasic symptoms. She notes a reduction in the intensity and length of the migraine attack symptoms which usually, but not always, follow the aura. Because she has lately suffered more than four migraine attacks per month, on the advice of her physician she continues daily dosing of 12.5-25 milligrams of rofecoxib over time. She then notes a substantial decrease in the frequency and intensity of the migraine attacks while continuing to take the rofecoxib tablets.

Example 13

A 55-year-old female patient with history of smoking, female hormone replacement therapy and frequent migraine in mid-life notes the onset of a recurrent scintillating scotoma lasting 15 to 30 minutes, but without headache (i.e., "acephalgic" migraine). Despite the lack of headache, these episodes are bothersome, provoke anxiety, and interfere with certain activities such as driving. The frequency is about twice per week. A cause other than migraine is not identified. The patient begins taking 12.5-25 milligrams of rofecoxib and 162.5-325 milligrams aspirin daily, or 12.5-25 milligrams rofecoxib on odd days alternating with 162.5-325 milligrams aspirin on even days. She notes a significant reduction in the frequency and intensity of the acephalgic migraine attacks while taking the medication over a period of several weeks to several months.

This invention may take on various modifications and alterations without departing from the spirit and scope thereof. Accordingly, it is to be understood that this invention is not to be limited to the above-described, but it is to be controlled by the limitations set forth in the following claims and any equivalents thereof. It is also to be understood that this invention may be suitably practiced in the absence of any element not specifically disclosed herein. In describing preferred embodiments of the invention, specific terminology is used for the sake of clarity. The invention, however, is not intended to be limited to the specific terms so selected, and it is to be understood that each term so selected includes all technical equivalents that operate similarly.

The invention claimed is:

1. A method for prophylactic treatment for migraine comprising regularly administering to a patient in need thereof a therapeutically effective amount of a combination consisting of:
a cyclooxygenase-2 inhibitor; and
a low dosage amount of acetylsalicylic acid or an active derivative having an anti-platelet effect.

2. The method of claim 1, wherein the cyclooxygenase-2 inhibitor and the acetylsalicylic acid or active derivative are administered in a single dosage unit.

3. The method of claim 1, wherein regular administration comprises once-daily administration of a dosage unit consisting of a cyclooxygenase-2 inhibitor and once-daily administration of a dosage unit consisting of acetylsalicylic acid or active derivative.

4. The method of claim 1, wherein regular administration comprises:
administration of a dosage unit consisting of a cyclooxygenase-2 inhibitor every other day; and
administration of a dosage unit consisting of acetylsalicylic acid or active derivative on days in which the dosage unit consisting of the cyclooxygenase-2 inhibitor is not administered.

5. The method of claim 1, wherein the cyclooxygenase-2 inhibitor is a compound of Formula II

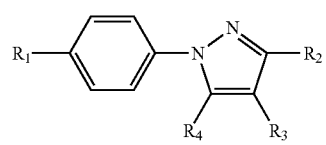

(II)

wherein:
$R_1$ is lower alkylsulfonyl or sulfamyl;
$R_2$ is alkyl, haloalkyl or halogen;
$R_3$ is hydrogen, lower alkyl or haloalkyl; and
$R_4$ is cycloalkyl, cycloalkenyl, aryl or substituted aryl.

6. The method of claim 5, wherein:
$R_1$ is sulfamyl;
$R_2$ is haloalkyl;
$R_3$ is hydrogen or lower alkyl; and
$R_4$ is aryl or substituted aryl.

7. The method of claim 6, wherein the cyclooxygenase-2 inhibitor is celecoxib.

8. The method of claim 7, wherein the therapeutically effective amount includes about 200 milligrams to about 400 milligrams celecoxib per day.

9. The method of claim 7, wherein the therapeutically effective amount includes about 200 milligrams celecoxib per day.

10. The method of claim 1, wherein the therapeutically effective amount includes about 50 to about 325 milligrams per day of acetylsalicylic acid or salicylate salt.

11. The method of claim 1, wherein the therapeutically effective amount includes about 325 milligrams per day of acetylsalicylic acid or salicylate salt.

12. A method for targeted prophylactic treatment of a migraine condition consisting essentially of:
determining a time window in which a patient desires to be free from migraine; and
administering to the patient, at a time prior to the determined time window, a therapeutically effective amount of a combination consisting of a cyclooxygenase-2 inhibitor and a low dosage amount of acetylsalicylic acid or an active derivative having an anti-platelet effect; to prevent or reduce migraine symptoms during the time window.

13. The method of claim 12, wherein the therapeutically effective amount includes about 50 to about 325 milligrams per day of acetylsalicylic acid or salicylate salt.

14. The method of claim 12, wherein the therapeutically effective amount includes about 325 milligrams per day acetylsalicylic acid or salicylate salt.

15. The method of claim 12, wherein the cyclooxygenase-2 inhibitor is a compound of Formula II

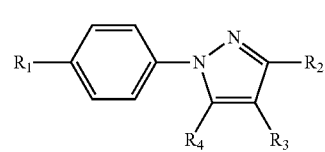

(II)

wherein:
$R_1$ is lower alkylsulfonyl or sulfamyl;
$R_2$ is alkyl, haloalkyl or halogen;
$R_3$ is hydrogen, lower alkyl or haloalkyl; and
$R_4$ is cycloalkyl, cycloalkenyl, aryl or substituted aryl.

16. The method of claim 15, wherein:
$R_1$ is sulfamyl;
$R_2$ is haloalkyl;
$R_3$ is hydrogen, or lower alkyl; and
$R_4$ is aryl or substituted aryl.

17. The method of claim 16, wherein the cyclooxygenase-2 inhibitor is celecoxib.

18. The method of claim 17, wherein the therapeutically effective amount includes about 200 milligrams celecoxib.

19. A pharmaceutical composition in unit dose form consisting of a therapeutically effective combination of a cyclooxygenase-2 inhibitor, a low dosage amount of acetylsalicylic acid or an active derivative having an anti-platelet effect, and a pharmaceutically acceptable carrier to prophylactically treat migraine.

20. The composition of claim 19, wherein the unit dose contains about 50 milligrams to about 325 milligrams of acetylsalicylic acid or salicylate salt.

21. The composition of claim 19, wherein the cyclooxygenase-2 inhibitor is a compound of Formula II

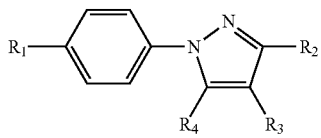

(II)

wherein:
$R_1$ is lower alkylsulfonyl or sulfamyl;
$R_2$ is alkyl, haloalkyl or halogen;
$R_3$ is hydrogen, lower alkyl or haloalkyl; and
$R_4$ is cycloalkyl, cycloalkenyl, aryl or substituted aryl.

22. The composition of claim 21, wherein:
$R_1$ is sulfamyl;
$R_2$ is haloalkyl;
$R_3$ is hydrogen, or lower alkyl; and
$R_4$ is aryl or substituted aryl.

23. The composition of claim 22, wherein the cyclooxygenase-2 inhibitor is celecoxib.

24. The composition of claim 23, wherein the unit dose contains about 200 milligrams celecoxib, and about 325 milligrams acetylsalicylic acid or salicylate salt.

25. A method for prophylactic treatment for migraine consisting of the steps of:
1) administering to a patient in need thereof a therapeutically effective amount of a dosage unit consisting of a cyclooxygenase-2 inhibitor every other day, wherein the cyclooxygenase-2 inhibitor does not have an anti-platelet effect and wherein the cyclooxygenase-2 inhibitor is a compound of Formula II

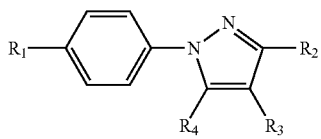

(II)

wherein:
$R_1$ is lower alkylsulfonyl or sulfamyl;
$R_2$ is alkyl, haloalkyl or halogen;
$R_3$ is hydrogen, lower alkyl or haloalkyl; and
$R_4$ is cycloalkyl, cycloalkenyl, aryl or substituted aryl; and 2) administering to a patient in need thereof a therapeutically effective amount of a dosage unit consisting of acetylsalicylic acid or an active derivative on days in which the dosage unit consisting of the cyclooxygenase-2 inhibitor is not administered, wherein the acetylsalicylic acid or active derivative has an irreversible anti-platelet effect;

wherein the administration on alternate days reduces undesired risks or overcomes the problems of side effects associated with the cyclooxygenase-2 inhibitor or the acetylsalicylic acid or active derivative.

26. The method of claim 25, wherein:
$R_1$ is sulfamyl;
$R_2$ is haloalkyl;
$R_3$ is hydrogen or lower alkyl; and
$R_4$ is aryl or substituted aryl.

27. The method of claim 26 wherein the cyclooxygenase-2 inhibitor is celecoxib.

28. The method of claim 25, wherein the therapeutically effective amount of the cyclooxygenase-2 inhibitor includes about 200 milligrams to about 400 milligrams celecoxib.

29. The method of claim 25, wherein the therapeutically effective amount of the cyclooxygenase-2 inhibitor includes about 200 milligrams celecoxib.

30. The method of claim 25, wherein the therapeutically effective amount of acetylsalicylic acid or an active derivative includes about 50 to about 325 milligrams acetylsalicylic acid or salicylate salt.

31. The method of claim 25, wherein the therapeutically effective amount of acetylsalicylic acid or an active derivative includes about 325 milligrams acetylsalicylic acid or salicylate salt.

* * * * *

UNITED STATES PATENT AND TRADEMARK OFFICE
CERTIFICATE OF CORRECTION

PATENT NO. : 8,680,081 B2  Page 1 of 1
APPLICATION NO. : 10/363079
DATED : March 25, 2014
INVENTOR(S) : Peter Van Patten It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3012 days.

Signed and Sealed this

Twenty-ninth Day of September, 2015

Michelle K. Lee
*Director of the United States Patent and Trademark Office*